(12) United States Patent
Schneider et al.

(10) Patent No.: US 6,500,377 B1
(45) Date of Patent: Dec. 31, 2002

(54) METHOD AND APPARATUS FOR ACTIVATING A MOVING WEB

(75) Inventors: Uwe Schneider, Rheinbach (DE); Christoph Johann Schmitz, Euskirchen-Stotzheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/674,693
(22) PCT Filed: May 7, 1999
(86) PCT No.: PCT/US99/10005
§ 371 (c)(1),
(2), (4) Date: Nov. 3, 2000
(87) PCT Pub. No.: WO99/56685
PCT Pub. Date: Nov. 11, 1999

(30) Foreign Application Priority Data

May 7, 1998 (EP) .............................. 98108920

(51) Int. Cl.⁷ ............................................... B29C 49/08
(52) U.S. Cl. ................ 264/288.4; 264/297.1; 100/76; 100/224; 223/61; 425/336; 425/409
(58) Field of Search ................. 28/172.2, 184; 100/353, 76, 82, 83, 138, 193, 237, 238, 240; 162/197, 196, 283, 287; 223/37, 61; 264/286, 288.4, 291, 299; 425/336, 339, 408, 409, 411; 604/358, 379, 385.201, 385.22, 385.23, 385.24, 396; 605/358, 379, 385.2, 385.22, 385.23, 385.24, 396

(56) References Cited

U.S. PATENT DOCUMENTS

| | | | |
|---|---|---|---|
| 3,860,003 A | 1/1975 | Buell | 128/287 |
| 3,929,135 A | 12/1975 | Thompson | 128/287 |
| 4,342,314 A | 8/1982 | Radel et al. | 128/287 |
| 4,463,045 A | 7/1984 | Ahr et al. | 428/131 |
| 4,609,518 A | 9/1986 | Curro et al. | 264/504 |
| 4,610,678 A | 9/1986 | Weisman et al. | 604/368 |
| 4,629,643 A | 12/1986 | Curro et al. | 428/131 |
| 4,673,402 A | 6/1987 | Weisman et al. | 604/368 |
| 4,834,735 A | 5/1989 | Alemany et al. | 604/368 |
| 4,834,741 A | 5/1989 | Sabee | 604/385.2 |
| 4,888,231 A | 12/1989 | Angstadt | 428/213 |
| 4,988,344 A | 1/1991 | Reising et al. | 604/368 |
| 4,988,345 A | 1/1991 | Reising | 604/368 |
| 5,006,394 A | 4/1991 | Baird | 428/138 |
| 5,143,679 A | 9/1992 | Weber et al. | 264/288.8 |
| 5,147,345 A | 9/1992 | Young et al. | 604/378 |
| 5,151,092 A | 9/1992 | Buell et al. | 604/385.2 |
| 5,221,274 A | 6/1993 | Buell et al. | 604/385.2 |

(List continued on next page.)

FOREIGN PATENT DOCUMENTS

| | | | |
|---|---|---|---|
| WO | WO 92/15445 | 9/1992 | B29C/55/18 |
| WO | WO 95/16746 | 6/1995 | C08L/67/02 |

*Primary Examiner*—Richard Crispino
*Assistant Examiner*—Sing Po Chan
(74) *Attorney, Agent, or Firm*—MIchael S. Kolodesh; Jay A. Krebs; Ken K. Patel

(57) ABSTRACT

A method and apparatus for activating a web, such as a web of interconnected disposable absorbent articles. The web is fed in a first direction to an activation system which includes a central disc and at least one outer disc. The central disc has a top surface and a pair of opposing side surfaces. The side surfaces of the central disc have activation tools located thereon while the outer disc includes complementary activation tools, The web is folded about the central disc such that a first zone of the web is positioned adjacent the top surface and a second zone of the web is positioned adjacent one of the side surfaces. The activation tool of the outer disc is then engaged with the activation tool of the central disc. The activation tool of the outer disc is then disengaged from the activation tool of the central disc. The activated web is then removed from the central disc.

20 Claims, 4 Drawing Sheets

U.S. PATENT DOCUMENTS

| | | | |
|---|---|---|---|
| 5,342,338 A | 8/1994 | Roe | 604/383 |
| 5,554,143 A | 9/1996 | Roe et al. | 604/385.2 |
| 5,554,144 A | 9/1996 | Roe et al. | 604/385 |
| 5,554,145 A | 9/1996 | Roe et al. | 604/385.2 |
| 5,556,394 A | 9/1996 | Roe et al. | 604/385.2 |
| 5,569,232 A | 10/1996 | Roe et al. | 604/385.2 |
| 5,571,096 A | 11/1996 | Dobrin et al. | 604/383 |
| 5,849,003 A * | 12/1998 | Olsen et al. | 604/385.03 |

* cited by examiner

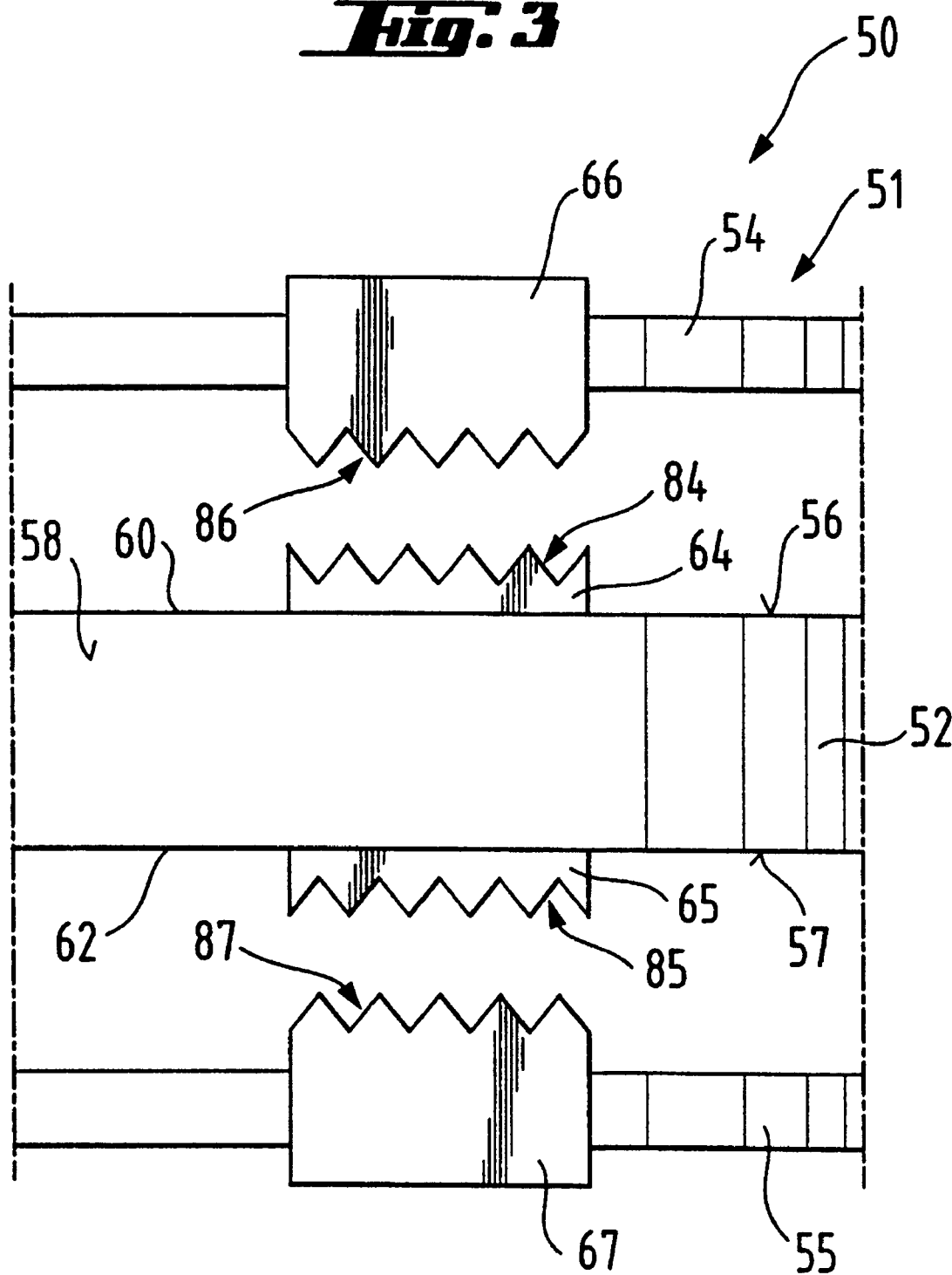

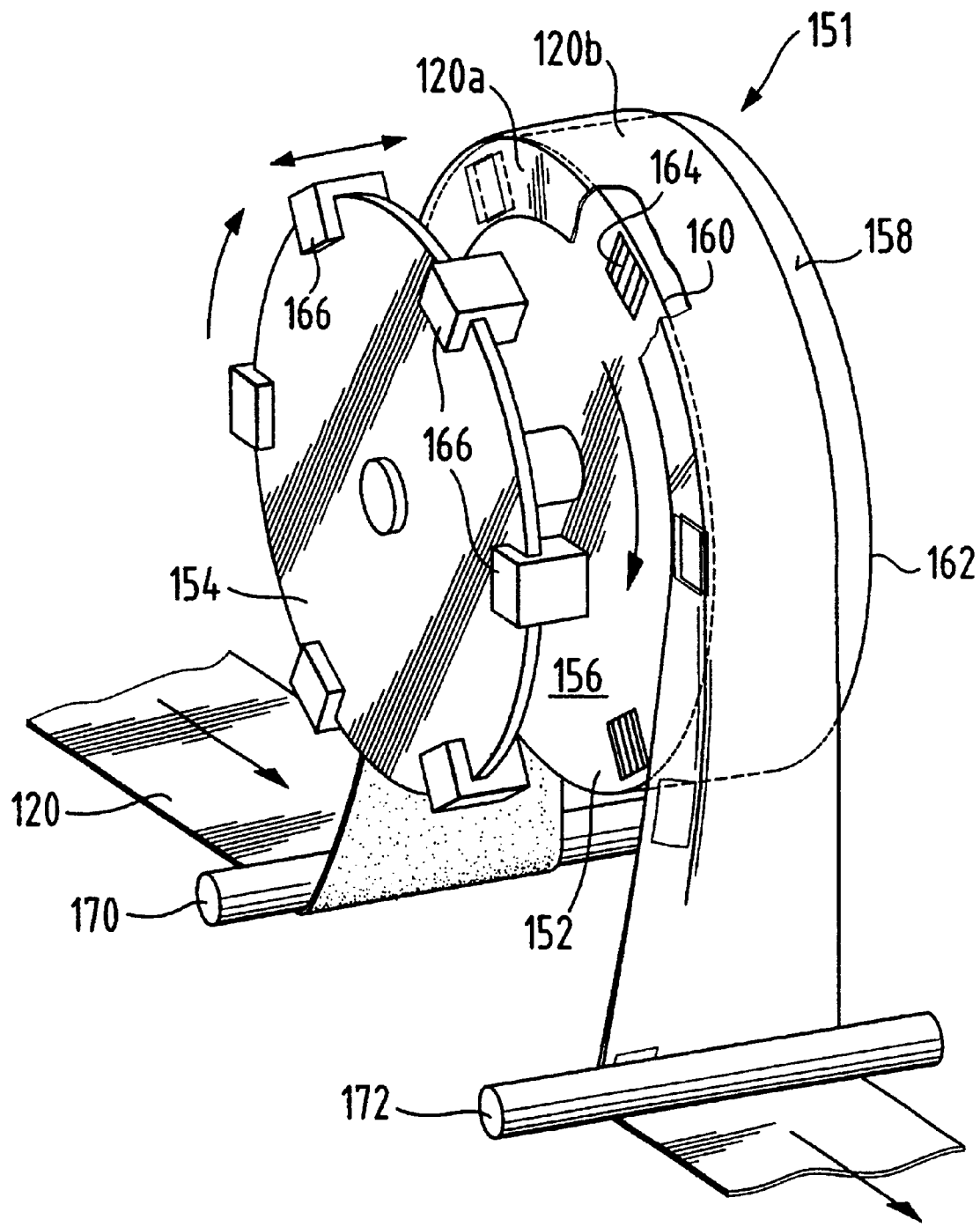

METHOD AND APPARATUS FOR ACTIVATING A MOVING WEB

FIELD OF THE INVENTION

The present invention relates to a method and apparatus for activating a moving web, such as a web of interconnected disposable absorbent articles, including disposable absorbent articles such as diapers, adult incontinence products, sanitary napkins and the like. More particularly, the invention relates to a method and apparatus for activating a moving web at a low strain rate while maintaining the line speed of the moving web.

BACKGROUND OF THE INVENTION

U.S. Pat. No. 4,834,741 issued to Sabee on May 30, 1989 discloses a single use garment, such a disposable diaper, comprising an untensioned elastomeric element secured between a pair of drawable elements in the waistband and legband portions. The elastic elements are affixed in the waistband portions of the diaper web while in a substantially relaxed condition to a drawable topsheet web, a drawable backsheet web or both. The portions of the diaper web containing the elastic elements are thereafter laterally stretched in the cross-machine direction by the meshing corrugations located on pairs of corrugated rolls. Simultaneously the coinciding portions of the drawable topsheet and backsheet webs in the area of the elastic element are incrementally stretched and drawn to impart a permanent elongation and molecular orientation thereto in the cross-machine direction. Because the corrugated rolls have their meshing corrugations aligned substantially parallel to the machine direction, the incremental stretching of the web takes place in the cross-machine direction. Accordingly, the fully processed waistband portions of the diaper web are thereafter elastically extensible in the cross-machine direction, at least to the point of initial stretching.

A similar operation is carried out with respect to the legbands, which include untensioned elastic elements, by passing the diaper web between another pair of meshing corrugated rolls. Because the corrugated rolls have their meshing corrugations aligned substantially parallel to the cross-machine direction, incremental stretching of the web takes place in the machine direction. Accordingly, the fully processed legband portions of the diaper web are thereafter elastically extensible in the machine direction, at least to the point of initial stretching.

While Sabee's suggestion to use corrugated rolls to incrementally stretch a laminate web have been found to work reasonably well when the desired degree of stretching is relatively small, it has been found that for higher degrees of incremental stretching there is a tendency for the corrugated rolls to cause damage to the web. In some situations, this damage can even take the form of rupturing the web potentially rendering the product unsuitable for its intended use. This problem becomes more and more serious as the speed of web processing and the desired degree of incremental stretching increase.

EP 573 587 attempted to solve the aforementioned problem of rupturing the web by sequentially stretching the web during the incremental stretching process. The stretching operation is carried out in stages by passing the web between multiple pairs of meshing corrugated rolls, each pair of rolls exhibiting a greater degree of meshing than the preceding pair, to sequentially stretch the web while minimizing the damage to the web. The use of multiple roll pairs with progressively greater degrees of meshing imposes a lower strain rate on the web than would be the case for a single pair of meshing corrugated rolls having an amplitude and degree of meshing comparable to the final pair of multiple rolls. Minimizing the strain rate reduces the tendency to cause damage to the web.

The problem with both of the above described methods is that the strain rate on the web remains to high and does not permit the desired degree of incremental stretching.

Accordingly, it is an object of the present invention to provide a method for incrementally stretching a web, i.e., activating a web, to a greater degree while minimizing damage to the web.

It is another object of the present invention to provide a method for incrementally stretching a web to a greater degree with less damage than has previously been obtainable with the meshing corrugated rolls of the prior art operating at comparable web speeds.

SUMMARY OF THE INVENTION

The present invention is directed to a method and apparatus for activating a web, such as a web of interconnected disposable absorbent articles, such as disposable diapers. The web is fed in a first direction to an activation system comprising a central disc and at least one outer disc. Preferably, the system comprises a central disc and a pair of outer discs. The central disc has a top surface and a pair of opposing side surfaces. At least one of the side surfaces of the central disc comprises at least one activation tool while the outer disc comprises at least one complementary activation tool. Preferably, each of the side surfaces of the central disc comprises an activation tool, more preferably, each of the side surfaces of the central disc comprises a plurality of activation tools. Similarly, it is preferred that each of the outer discs comprise a plurality of complementary activation tools. The web is then folded about the central disc such that a first zone of the web is positioned adjacent the top surface and a second zone of the web is positioned adjacent the side surface. In some embodiments, it may be desired to fold the web about the central disc in a U-like configuration such that a pair of second zones of the web are positioned adjacent the side surfaces of the central disc. The activation tool of the outer disc is engaged with the activation tool of the central disc. The activation tool of the outer disc is disengaged from the activation tool of the central disc. The activated web is then removed from the central disc.

The activation tool of the outer disc may be engaged with the activation tool of the central disc by moving the activation tool of the outer disc inwardly toward the activation tool of the central disc. Alternatively, or in combination with the former, the activation tool of the outer disc may be engaged with the activation tool of the central disc by moving the activation tool of the central disc outwardly toward the activation tool of the outer disc.

The activation tool of the outer disc may be disengaged from the activation tool of the central disc by moving the activation tool of the outer disc outwardly away from the activation tool of the central disc. Alternatively, or in combination with the former, the activation tool of the outer disc may be disengaged from the activation tool of the central disc by moving the activation tool of the central disc inwardly away from the activation tool of the outer disc.

The activation tools preferably comprise corrugations or grooves. Of course other activation tools may be used.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

FIG. 3 is a top sectional illustration of a portion of the incremental web stretching system of FIG. 2, with the web being completely removed.

FIG. 4 is a simplified perspective illustration of an alternative embodiment of an incremental web stretching system of the present invention.

DETAILED DESCRIPTION OF THE INVENTION

It will be readily apparent to those skilled in the art that although the following description of the present invention is in connection with a single use diaper structure having preselected elasticized areas, the present invention may be practiced with equal facility on nearly any web.

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner.

Figure 1:
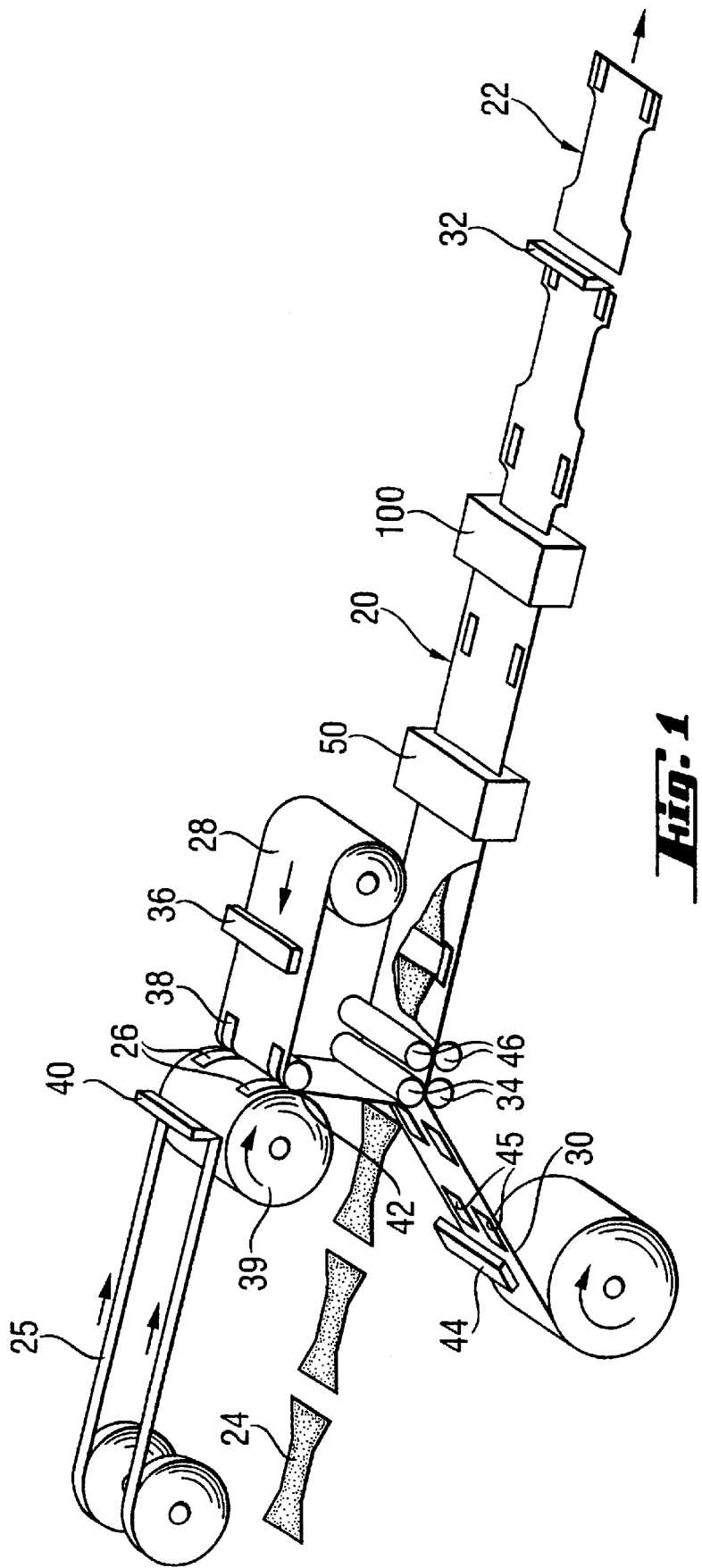
FIG. 1 is a simplified perspective illustration showing the assembly of a web of single use diapers.

A diaper manufacturing process of the present invention is schematically illustrated in FIG. 1. Suitable configurations for the diapers illustrated in FIG. 1 are described generally in U.S. Pat. No. 3,860,003 which issued to Kenneth B. Buell on Jan. 14, 1975; U.S. Pat. No. 5,151,092 issued to Buell on Sep. 9, 1992; U.S. Pat. No. 5,221,274 issued to Buell on Jun. 22, 1993; U.S. Pat. No. 5,569,232 which issued to Roe et al. on Oct. 29, 1996; U.S. Pat. No. 5,554,144 which issued to Roe et al. on Sep. 10, 1996; U.S. Pat. No. 5,554,143 which issued to Roe et al. on Sep. 10, 1996; U.S. Pat. No. 5,554,145 which issued to Roe et al. on Sep. 10, 1996; and U.S. Pat. No. 5,556,394 which issued to Roe et al. on Sep. 17, 1996.

Referring to FIG. 1, there is shown a continuous web 20 comprised of a plurality of interconnected single use disposable absorbent articles, such as diapers 22. Each diaper 22 is comprised of an absorbent pad element or absorbent core 24, a pair of elastomeric elements or patches 26, which may be comprised of "live" synthetic or natural rubber, synthetic or natural rubber foam, elastomeric film, elastomeric nonwoven laminate, elastomeric scrim or the like, or other materials or combinations of materials commonly used for such purposes. The absorbent pad elements 24 and the elastomeric elements 26 being located intermediate a backsheet 28 and a topsheet 30.

The backsheet 28 is generally that portion of the diaper which prevents the exudates absorbed and contained therein from soiling articles which may contact the diaper, such as bedsheets and undergarments. In preferred embodiments, the backsheet 28 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper while still preventing exudates from passing through the backsheet. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096.

The topsheet 30 is preferably compliant, soft feeling, and non-irritating to the wearer's skin. Further, at least a portion of the topsheet 30 is liquid pervious, permitting liquids to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wet-laid, meltblown, hydroentangled, or otherwise processed as is known in the art. One suitable topsheet comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135; U.S. Pat. No. 4,342,314; U.S. Pat. No. 4,463,045; U.S. Pat. No. 5,006,394; U.S. Pat. No. 4,609,518; and U.S. Pat. No. 4,629,643.

Preferably, the topsheet is made of a hydrophobic material or is treated to be hydrophobic in order to isolate the wearer's skin from liquids contained in the absorbent pad. If the topsheet is made of a hydrophobic material, preferably at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent pad. The topsheet can be rendered hydrophilic by treating it with a surfactant or by incorporating a surfactant into the topsheet. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 and U.S. Pat. No. 4,988,345.

The continuous webs of backsheet material 28 and topsheet material 30 are preferably maintained under very slight tension in the machine direction to prevent wrinkling and to facilitate registration with the diaper assembly and converting operations until the completed diaper web is severed into discrete diapers 22 at knife 32.

The absorbent pad segments 24 are fed into the nip between a pair of combining or laminating rolls 34 at regularly spaced, predetermined intervals. The absorbent pads 24 may comprise any absorbent material which is generally compressible, conformable, non-irritating to the wearer's skin, and capable of absorbing and retaining liquids such as urine and other certain body exudates. The absorbent pads 24 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent pad 24 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent pad 24 should be compatible with the design loading and the intended use of the diaper 20. Exemplary absorbent structures for use as the absorbent pads are described in U.S. Pat. No. 4,610,678; U.S. Pat. No. 4,673,402; U.S. Pat. No. 4,834,735; U.S. Pat. No. 4,888,231; U.S. Pat. No. 5,147,345; and U.S. Pat. No. 5,342,338.

The elastomeric patches 26 may be secured to the backsheet 28, topsheet 30 or both utilizing either an intermittent bonding configuration or a substantially continuous bonding configuration. The intermittent bonding configuration is normally desirable in those situations where a relatively high degree of z-direction bulking is desired in the finished product. Conversely, a continuous bonding configuration has been found desirable where a relatively lower degree of z-direction bulking is desired in the finished product.

The web of backsheet material 28 is directed in close proximity to a glue applicator 36. The glue or adhesive 38 may be heated or unheated. If an intermittent bonding pattern is desired the glue applicator 36 may be used to apply discrete, spaced apart spots, lines, or spirals of adhesive in the predetermined areas of the backsheet 28 where the substantially untensioned elastomeric patches 26 will be placed.

Alternatively, if a substantially continuous bonding pattern is desired the glue applicator may be used to apply a substantially uniform and continuous application of adhesive 38 to the backsheet 28 in those predetermined areas of the backsheet 28 where the substantially untensioned elastomeric patches 26 will be placed.

Instead of using an adhesive, the backsheet 28 and/or topsheet 30 may be bonded to the elastomeric patches 26 using heat bonding, pressure bonding, ultrasonic bonding, etc. In such instances, thermal energy may, if desired, be applied to the backsheet 28 by other means well known to those skilled in the art, e.g., radiant heaters, hot air blasts, etc., to achieve a similar result.

Two rolls of elastomeric material 25 are fed under very slight (essentially "zero strain") tension at a speed which provides the desired length of elastomeric patch 26 per diaper onto an anvil roll 39 equipped with vacuum hold down ports (not shown) at its periphery. Knife 40 makes one cut per diaper and the substantially untensioned elastomeric patches 26 travel with anvil roll 39 secured to its periphery by vacuum until they reach transfer point 42. At point 42 the elastomeric patches 26 are transferred to predetermined portions of the backsheet web 28 coinciding with adhesive 38. The transfer is sequential and the surface speed of the vacuum equipped anvil roll 39 and the backsheet web 28 are essentially equal.

The backsheet web 28 with elastomeric patches 26 attached thereto at predetermined points along its length is then directed to the pair of laminating or combining rolls 34.

A continuous web of topsheet material 30 is directed in close proximity to a second glue applicator 44 where a pattern of adhesive 45 sized to substantially match the dimensions and locations of the elastomeric patches 26 on backsheet web 28 is preferably applied. As with backsheet material 28, the pattern of adhesive applied to the topsheet material 30 may be either intermittent or substantially continuous. If desired, adhesive applicator 44 may be identical to adhesive applicator 36.

The backsheet web 28 and the topsheet web 30 and the absorbent pads 24 are brought into contact with one another at combining rolls 34. Just prior to the webs and pads coming into contact with one another, additional adhesive is preferably applied to one or both webs by means which are, for clarity, not shown in FIG. 1. The latter adhesive secures predetermined portions of the backsheet, topsheet and absorbent pad to one another to form the diaper web 20.

The fully assembled diaper web 20 thereafter preferably proceeds through a pair of bond setting rolls 46, which may require chilling to minimize glue bleed through.

The fully assembled diaper web 20 is then directed through an activation system of the present invention, which is shown schematically as 50 in FIG. 1. Details of a particularly preferred activation system of the present invention which can be employed as system 50 are set forth in FIG. 2.

Figure 2:
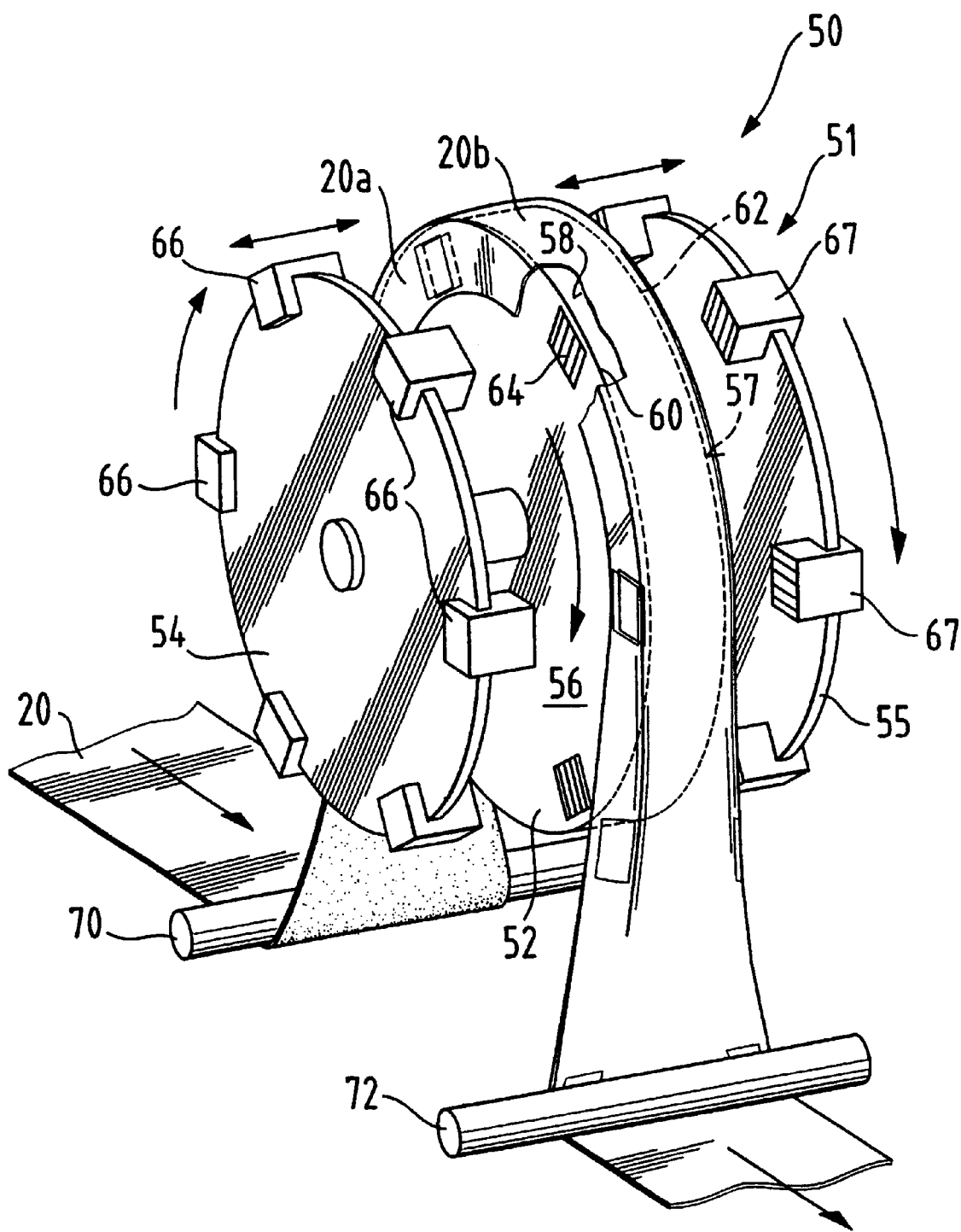
FIG. 2 is a simplified perspective illustration of an incremental web stretching system of the present invention.

Referring now to FIGS. 2 and 3, an incremental web stretching system 51 is exemplified as the activation system 50. Incremental web stretching system 51 of FIGS. 2 and 3 comprises a central roll or disc 52 and two outer rolls or discs 54, 55. The discs 52, 54, and 55 rotate in the direction indicated by the arrows associated therewith. Incremental web stretching system 51 is shown in FIGS. 2 and 3 as comprising two outer discs 54 and 55, however, in some instances it may be desirable to have only one outer disc. For example, in some situations it may be desirable to activate only one side or edge of the web and not the opposing side. In such situations, there would only be a need for one outer disc.

Central disc 52 has a first side surface 56 and an opposing second side surface 57. A top surface 58 spans the distance between side surfaces 56 and 57. Edge 60 connects top surface 58 with side surface 56 while edge 62 connects top surface 58 with side surface 57. A portion of the diaper web 20 has been cut away in FIG. 2 to reveal the configuration of the central disc 52.

In FIGS. 2 and 3, side surfaces 56 and 57 are shown to be perpendicular with top surface 58. However, side surfaces 56 and 57 may be angled relative to top surface 58 at an angle other than 90°. For example, side surfaces 56 and 57 may be angled relative to top surface 58 at an angle ranging from 100 to 90°. Most preferably, side surfaces 56 and 57 are angled relative to top surface 58 at an angle of 90°.

The overall dimensions of the respective discs can be selected as desired. The width of the top surface 58 can be very small, e.g., 1 cm or less, or may be quite large. The diameters of the respective discs can be of any desired dimension. As the diameter of the disc is increased the relative time to activate the web also increases.

A plurality of activation tools 64 are located on side surface 56 of central disc 52. Similarly, a plurality of activation tools 65, are located on side surface 57 of central disc 52. The number, size, spacing, shape, configuration, etc. of activation tools on central disc 52 can be selected by the diaper designer as desired. Outer discs 54 and 55 comprise a plurality of activation tools 66 and 67, respectively, which interact with activation tools 64 and 65 on central disc 52. The number, size, spacing, shape, configuration, etc. of activation tools on outer discs 54 and 55 can be selected by the diaper designer to produce the desired effects.

As can be seen in FIG. 2, as diaper web 20 is fed past roller 70 and onto central disc 52, portions of the web are folded over the edges 60 and 62 of central disc 52. Conventional folding equipment, such as folding boards, may be utilized to fold web 20 over the edges 60 and 62 of central disc 52. Once folded about central disc 52, the web has at least two distinct zones or regions, a first zone 20b positioned adjacent top surface 58 and a pair of second zones 20a positioned adjacent side surfaces 56 and 57 respectively,. The second zones 20a are preferably held against side surfaces 56 and 57. Preferably, the second zones 20a of the web 20 are held against side surfaces 56 and 57 by vacuum ports (not shown).

Upon infeed of the diaper web 20 onto the central disc 52 the activation tools 66 and 67 are spaced apart to provide clearance for the incoming web 20. When the web is folded onto central disc 52 and second zones 20a are held against side surfaces 56 and 57, activation tools 66 and 67 are caused to engage with activation tools 64 and 65 on central disc 52. To cause engagement of the respective tools, the activation tools of the outer discs may be moved inwardly towards the activation tools of the central disc, while the tools of the central disc remain stationary. Alternatively, the activation tools of the central disc may be moved outwardly towards the activation tools of the outer disc, while the tools of the outer discs remain stationary. In another embodiment, the activation tools of the outer discs may be moved inwardly and simultaneously the activation tools of the central disc may be moved outwardly to cause engagement of the tools.

When the desired activation has been achieved the activation tools are disengaged from one another. To cause disengagement of the respective tools, the activation tools of the outer discs may be moved outwardly away from the activation tools of the central disc, while the tools of the central disc remain stationary. Alternatively, the activation tools of the central disc may be moved inwardly away from the activation tools of the outer disc, while the tools of the outer discs remain stationary. In another embodiment, the activation tools of the outer discs may be moved outwardly and simultaneously the activation tools of the central disc may be moved inwardly to cause disengagement of the tools.

The activated web 20 is then removed from central disc 52 and travels past roller 72.

Because the second zones 20a of web 20 are folded about central disc 52 onto side surfaces 56 and 57, the time allowed to activate the second zones 20a is dramatically increased compared to that of first zone 20b. As the time allowed for activation is increased, a lower strain is imparted on the web 20 thus reducing the potential for web damage. This is believed to be due to the fact that as the incremental stretching operation is carried out more slowly, the web is stretched gradually. The present invention may result in reducing the strain rate activation over prior art systems by as much as 25%, 50% 100% or even more.

Referring now to FIG. 3, there is shown a top sectional view of a portion of the incremental web stretching system 51 with the web 20 not shown for clarity. Activation tools 64, 65, 66 and 67 each comprise corrugations or grooves 84, 85, 86 and 87, respectively. The exact configuration, orientation, spacing and depth of the complementary grooves 84, 85, 86 and 87 on the tools 64, 65, 66 and 67 may be varied depending upon such factors as the amount of elasticity desired in the portions of the diaper web comprising the elastomeric patches 26. The degree or depth of engagement of the opposing peaks on the tools may of course also be adjusted, as desired, to produce more or less extensibility in the diaper web.

Referring now to FIG. 2, timing of the web 20 containing elastomeric patches 26 is such that the elastomeric patches contained within the diaper web 20 coincide with pairs of activation tools 64, 66 and 65, 67, respectively, as the diaper web 20 travels through activation system 50. If desired, the activation tools may be of greater overall dimension than that of elastomeric patches 26 so as to impart a degree of extensibility to those portions of the topsheet and backsheet which are adjacent to the elastomeric patches 26.

Following the activation operation shown schematically as 50 in FIG. 1, the fully assembled diaper web 20 is preferably passed through a side notching apparatus shown schematically as 100, wherein notches intended to coincide with the wearer's legs are cut from the lateral edge portions of the fully assemble diaper web.

Finally, the diaper web 20 is cut at predetermined locations along its length by means of knife 32 to produce single use diapers 22 having at least one pair of elastically extensible side panels.

From the description contained herein, it is clear that the improved method of the present invention may be employed to advantage to produce a wide range of elasticized articles.

The activation tools shown in FIG. 3 may be of numerous configurations. For example, the corrugations on each of the activation tools need not all be oriented parallel to one another. Furthermore, the corrugations may be oriented in any direction. The corrugations may be straight, zig-zag, curvilinear, etc.

In order for the web 20 to be held flat against side surfaces 56 and 57 of disc 52, it will have folds or creased portions within the second zone 20a. While the folded portions within second zone 20a may be activated, it is preferred that the non-folded portions be activated. Of course, once the non-folded portions have been activated, they may then be folded, and the previously folded portions may now unfolded to lie flat against the side surfaces 56 and 57 such that they may be activated in a flat condition. Such a technique allows the entire second zone 20a of the web to be activated while in a flat non-folded condition.

Referring now to FIG. 4, there is illustrated another embodiment of an incremental web stretching system 151 of the present invention. Incremental web stretching system 151 of FIG. 4 comprises a first disc 152 and a second disc 154. The discs 152 and 154 rotate in the direction indicated by the arrows associated therewith.

Disc 152 has a first side surface 156 and an opposing second side surface 157, (not shown in FIG. 4). A top surface 158 spans the distance between side surfaces 156 and 157. Edge 160 connects top surface 158 with side surface 156 while edge 162 connects top surface 158 with side surface 157. A portion of the diaper web 120 has been cut away in FIG. 4 to reveal the configuration of disc 152.

A plurality of activation tools 164 are located on side surface 156 of disc 152. The number, size, spacing, shape, configuration, etc. of activation tools on disc 152 can be selected by the diaper designer to produce the desired effects. Disc 154 comprises a plurality of activation tools 166 which interact with activation tools 164 on disc 152. The number, size, spacing, shape, configuration, etc. of activation tools on disc 154 can be selected by the diaper designer to produce the desired effects.

As can be seen in FIG. 4, as diaper web 120 is fed past roller 170 and onto disc 152, portions of the web are folded over the edge 160 but not over edge 162 of disc 152. Conventional folding equipment, such as folding boards, may be utilized to fold web 120 over edge 160. Once folded about disc 152, the web has at least two distinct zones or regions, a first zone 120b positioned adjacent top surface 158 and a single second zone 120a positioned adjacent side surface 156. The second zone 120a is preferably held against side surface 156. Preferably, the second zone 120a of the web 120 is held against side surface 156 by vacuum ports (not shown).

Upon infeed of the diaper web 120 onto the disc 152 the activation tools 166 are spaced apart to provide clearance for the incoming web 120. When the web is folded onto central disc 152 and second zone 120a is held against side surface 156, activation tools 166 are caused to engage with activation tools 164 on disc 152. When the desired activation has been achieved the activation tools are disengaged from one another. The activated web is then removed from disc 152 and travels past roller 172.

A series of sequential activation systems may also be utilized. For example, a series of activation systems may be used to carry out different activations or similar activations on other portions of the web. For example, one may be used to activate an elastomeric member such as shown in FIGS. 2–4, one may be used to puncture or aperture the web, one may be used to cut side notches in the web for leg openings. Of course, other types of activation tools may also be utilized.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for activating a web, said method comprising the steps of:
    a) feeding a web in a first direction to an activation system, said system comprising a central disc and at least one outer disc, said central disc having a top surface and a pair of opposing side surfaces, at least one of said side surfaces comprising at least one activation tool, said outer disc comprising at least one complementary activation tool;
    b) folding said web about said central disc such that a first zone of said web is positioned adjacent said top surface and a second zone of said web is positioned adjacent one of said side surfaces such that said second zone of said web is at least partially overlapping said activation tool of one of said side surfaces of said central disc;
    c) engaging said activation tool of said outer disc with said activation tool of said central disc;
    d) disengaging said activation tool of said outer disc from said activation tool of said central disc; and
    e) removing said web from said central disc.

2. The method of claim 1, wherein said web is folded about said central disc such that a second zone is positioned adjacent both of said side surfaces.

3. The method of claim 2, wherein said activation system comprises a central disc and a pair of outer discs.

4. The method of claim 3, wherein each of said side surfaces of said central disc comprises at least one activation tool.

5. The method of claim 4, wherein each of said side surfaces of said central disc comprises a plurality of activation tools.

6. The method of claim 5, wherein each of said outer discs comprises a plurality of activation tools.

7. The method claim 1, wherein said activation tool of said outer disc is engaged with said activation tool of said central disc by moving said activation tool of said outer disc inwardly toward said activation tool of said central disc.

8. The method of claim 1, wherein said activation tool of said outer disc is disengaged from said activation tool of said central disc by moving said activation tool of said outer disc outwardly away from said activation tool of said central disc.

9. The method of claim 1, wherein said activation tool of said outer disc is engaged with said activation tool of said central disc by moving said activation tool of said central disc outwardly toward said activation tool of said outer disc.

10. The method of claim 1, wherein said activation tool of said outer disc is disengaged from said activation tool of said central disc by moving said activation tool of said central disc inwardly away from said activation tool of said outer disc.

11. The method of claim 1, wherein said activation tools comprise corrugations or grooves.

12. The method of claim 1, wherein said web comprises a plurality of interconnected single use disposable absorbent articles.

13. The method of claim 12, wherein said disposable absorbent articles comprise disposable diapers.

14. An apparatus for activating a web, said apparatus comprising:
    a) a central disc and at least one outer disc, said central disc having a top surface and a pair of opposing side surfaces, at least one of said side surfaces comprising at least one activation tool, said outer disc comprising at least one complementary activation tool;
    b) means for feeding a web onto said central disc;
    c) means for folding said web about said central disc such that a first zone of said web is positioned adjacent said top surface and a second zone of said web is positioned adjacent one of said side surfaces;

d) means for causing said activation tool of said outer disc to engage said activation tool of said central disc;

e) means for causing said activation tool of said outer disc to disengage said activation tool of said central disc; and f) means for removing said web from said central disc.

15. The apparatus of claim 14, wherein said activation system comprises a central disc and a pair of outer discs.

16. The apparatus of claim 15, further comprising means for folding said web about said central disc such that a second zone is positioned adjacent both of said side surfaces.

17. The apparatus of either claim 15 or claim 16, wherein each of said side surfaces of said central disc comprises at least one activation tool.

18. The apparatus of claim 17, wherein each of said side surfaces of said central disc comprises a plurality of activation tools.

19. The apparatus of 18, wherein each of said outer discs comprises a plurality of activation tools.

20. The apparatus of claim 14, wherein said activation tools comprise corrugations or grooves.

\* \* \* \* \*